(12) United States Patent
Nielles-Vallespin et al.

(10) Patent No.: US 8,055,048 B2
(45) Date of Patent: Nov. 8, 2011

(54) METHOD FOR GENERATION OF TEMPORALLY HIGH-RESOLUTION MR EXPOSURES

(75) Inventors: Sonia Nielles-Vallespin, Nürnberg (DE); Peter Schmitt, Weisendorf (DE); Peter Speier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 926 days.

(21) Appl. No.: 12/037,218

(22) Filed: Feb. 26, 2008

(65) Prior Publication Data

US 2008/0205735 A1 Aug. 28, 2008

(30) Foreign Application Priority Data

Feb. 26, 2007 (DE) .......... 10 2007 009 209

(51) Int. Cl.
*A61B 5/055* (2006.01)
*G06K 9/60* (2006.01)

(52) U.S. Cl. .......... 382/131; 324/307; 600/410

(58) Field of Classification Search .......... 382/128, 382/130, 131; 324/307–315; 600/410–423
See application file for complete search history.

(56) References Cited

U.S. PATENT DOCUMENTS

| | | | |
|---|---|---|---|
| 4,991,092 A | 2/1991 | Greensite | |
| 5,933,006 A | 8/1999 | Rasche et al. | |
| 5,953,463 A | 9/1999 | Tanaka et al. | |
| 2002/0183612 A1 | 12/2002 | Deimling | |
| 2006/0062486 A1 | 3/2006 | Lee et al. | |
| 2007/0010731 A1* | 1/2007 | Mistretta | 600/407 |
| 2008/0063247 A1* | 3/2008 | Griswold | 382/128 |
| 2010/0034447 A1* | 2/2010 | Geier et al. | 382/131 |

FOREIGN PATENT DOCUMENTS

EP 0 627 633 A1 12/1994

OTHER PUBLICATIONS

Mistretta et. al. "Highly Constrained Backprojection for Time Resolved MRI", Magnetic Resonance in Medicine, vol. 55 (2005) pp. 30-40.*

"Highly Constrained Backprojection for Time-Resolved MRI," Mistretta et al., Magnetic Resonance in Medicine, vol. 55 (2005) pp. 30-40.

* cited by examiner

*Primary Examiner* — Robert Kim
*Assistant Examiner* — David E Smith
(74) *Attorney, Agent, or Firm* — Schiff Hardin LLP

(57) ABSTRACT

In a method for generation of MR exposures in an MR system, a number of under-sampled MR raw data sets are acquired with non-constant density in k-space. A density compensation is implemented dependent on the geometry of the structure to be depicted. The under-sampled MR raw data sets are translated into a Cartesian coordinate system. Fourier transformation of the translated raw data sets in classical three-dimensional space ensues to generate under-sampled MR images. An averaged MR image is generated on the basis of a number of the under-sampled MR raw data sets. The MR exposures are produced by multiplication of the under-sampled MR images with the averaged MR image.

16 Claims, 3 Drawing Sheets

METHOD FOR GENERATION OF TEMPORALLY HIGH-RESOLUTION MR EXPOSURES

BACKGROUND OF THE INVENTION

1. Field of the Invention

The present invention concerns a method for generation of temporally high-resolution MR exposures in a magnetic resonance system. The present application can in particular (but not exclusively) be used for generation of angiographic exposures by nuclear magnetic resonance.

2. Description of the Prior Art

In most MR applications it is desirable to obtain a high spatial resolution in the acquired MR images without extending the acquisition time too much. However, if the MR raw data set is acquired while adhering to the Nyquist condition (which means that the sampling rate is twice as high as the limit frequency to be depicted), the acquisition time automatically extends with increased spatial resolution since more raw data points must be collected in k-space.

In addition to the typical MR acquisition techniques, radially symmetrical k-space data acquisition techniques have also been used in order to accelerate the raw data acquisition overall.

A method in which radial k-space acquisition techniques are used for generation of angiography exposures is described in "Highly Constrained Backprojection for Time-Resolved MRI" by C. A. Mistretta in Magnetic Resonance in Medicine 55: pages 30-40 (2006). A number of under-sampled MR raw data is acquired with various radial projections. The different under-sampled raw data are added and a spatially high-resolution angiography image is generated by a filtered back-projection. An unfiltered back-projection is likewise implemented for each acquisition raw data set, wherein after normalization of the signal intensity the individual under-sampled MR images are multiplied with the averaged MR image in order to acquire a number of temporally high-resolution MR images overall. However, this method exhibits a number of disadvantages. For example, the calculation of the back-projection limits the application of this described method to radial acquisition techniques. The application of this method to other acquisition techniques (such as, for example, helical acquisition techniques or other acquisition techniques) is not possible. Furthermore, the method includes the step of calculating the back-projection from the averaged MR image that is in a Cartesian coordinate system. This method step is complex and very time-consuming.

SUMMARY OF THE INVENTION

An object of the present invention is to provide a method for generation of high-resolution MR exposures that likewise enables temporally high-resolution MR exposures with acceptable spatial resolution, which is simple and usable for many acquisition techniques.

This object is achieved in accordance with the invention by a method for generation of MR exposures in an MR system in which a number of under-sampled MR raw data sets are acquired with non-constant density in k-space. Furthermore, a density compensation of the under-sampled MR raw data sets ensues wherein the density compensation is selected dependent on the geometric structure of the anatomy or structure to be depicted. This means that the density compensation can be varied in corresponding to the anatomy or structure to be depicted. In a further step, the under-sampled MR raw data sets are transferred into a Cartesian coordinate system. After the implementation of the translation into a Cartesian coordinate system (known as the regridding), Fourier transformation of the raw data ensues in classical three-dimensional space to generate under-sampled MR images. In a further step, an averaged MR image is generated on the basis of the acquired under-sampled MR raw data sets. Temporally high-resolution MR exposures can now be generated by multiplying the under-sampled MR images with the averaged MR image. The basis of the invention is that (particularly in angiography exposures) the vessels to be shown are only sparsely distributed in space (i.e., in the image). This means that there is essentially no signal between the vessels to be depicted. From this, it follows that it is possible to depict this vessel or the anatomy to be depicted with an image that has a broad point spread function. In general, the use of under-sampled MR raw data widens the point spread function. It is consequently possible to acquire the time-dependent signal intensities with significantly under-sampled data. The position of the geometry to be depicted (for example of the vessel) is determined by the averaged MR image that is based on a number of under-sampled MR raw data sets. Temporally high-resolution MR images can now be generated by the individual under-sampled MR images (calculated from the under-sampled MR raw data sets) being multiplied with the averaged MR image. The complexity of the method according to the prior art is primarily due to the fact that this is the idea that the individual temporally high-resolution MR images representing a dynamic weighting coefficient of the individual images. However, this weighting coefficient is not necessary since the MR image is not based on a specific intensity scale. According to the present invention it is only necessary to generate a contrast that separates the background without signal and the vessels. The calculation of the back-projection of the data from the determined MR image thus can be foregone. In the aforementioned prior art by C. A. Mistretta, a normalization of the unfiltered projections of the individual images was implemented by division of the unfiltered projections calculated back from the reference image. Instead of such a back-projection, a regridding is implemented in accordance with the invention, meaning that the data acquired with non-constant density in k-space are carried over into a Cartesian coordinate system wherein the transformation into the image space (image domain) is subsequently possible by fast Fourier transformation methods. According to a further important aspect of the invention, the density compensation varies dependent on the structure of the anatomy to be depicted (such as, for example, the structure of the vessels to be depicted).

The inventive method is applicable in many ways since it is not limited to radial k-space acquisition techniques like the method according to the prior art. Furthermore, the inventive method foregoes the aforementioned calculation of the back-projections of the data, so the image calculation is simplified since the back-calculation of the projections is mathematically very complicated. A further aspect of the invention is based on the fact that the density weighting is selected dependent on the anatomy to be depicted.

In a preferred embodiment, the method is used for production of angiography exposures, the method being particularly suited for use in contrast agent-intensified angiography. In contrast agent-intensified angiography acquisitions it is important to reliably detect the course of the contrast agent in the individual vessel branches. The representation of the arteries in static angiography exposures is generally desirable. The image acquisition must therefore be limited to the time before the return flow of the contrast agent through the veins. The present invention is primarily applied in dynamic angiographies where the flow of the contrast agent through the arteries (and veins) is temporally resolved. In this case the data acquisition can additionally be extended to the venous phase. The reference image then includes both vessel types. The vessels are then separated by multiplication with the under-sampled MR images. For arteries and veins lying close to one another it can naturally be helpful to suppress the veins in the reference image, by reconstructing the reference image only from a limited number of under-sampled MR raw data sets, although this naturally negatively affects the image quality.

The MR raw data sets are advantageously acquired in k-space with radial projections, with different radial projections being used for various under-sampled MR raw data sets. By the use of different radial projections for the individual raw data sets, an averaged, high-resolution data set can subsequently be obtained by summation. This averaged, high-resolution data set is the basis for the averaged MR image that is required in turn for the multiplication with the temporally high-resolution under-sampled MR images.

The density compensation advantageously ensues before the translation of the raw data sets in a Cartesian coordinate system. In acquisitions of k-space with non-constant density it is generally possible to implement the density, compensation before or after the translation operation in a Cartesian coordinate system. It is preferable, however, for the density compensation to be executed before the regridding operation is implemented. After the translation of the data sets into a Cartesian coordinate system, the density compensation is for the most part only possible to a satisfactory extent when the rate of change of the density in k-space is not too large. Particularly in the case of radially acquired data sets, however, the density change in proximity to the k-space center is relatively large, so that for radially acquired data sets, the density compensation advantageously ensues before the translation of the raw data sets in a Cartesian coordinate system.

Furthermore, the density compensation and conversion into a Cartesian coordinate system advantageously ensues in k-space so that a more homogeneous Cartesian raw data set exists to which fast Fourier transformation algorithms can be applied. This significantly accelerates the calculation of the MR image data and shortens overall the computation times for calculation of the MR images.

The intensities of the vessels in the temporally high-resolution MR images that result from the multiplication of the under-sampled MR image with the averaged MR image are proportional to the average intensity squared. For example, an essentially linear intensity scale can be achieved on the MR image to be depicted by root generation of the product. However, any other non-linear scaling is also possible for the depiction of the MR exposures.

A density compensation function can be used for density compensation, wherein the slopes of the density compensation function are varied dependent on the vessel structure or anatomy to be depicted. The point spread function in the temporally high-resolution MR images can be adapted to the vessel structure to be depicted. For vessel structures lying close to one another, for example, a narrow point spread function is necessary in order to be able to show the intensity curves in the two vessels separate from one another. This point spread function can be influenced by variation of the density compensation function. The signal-to-noise ratio in the image is amplified and the under-sampling artifacts are reduced by a reduction of the slope of the density compensation function; however, the spatial resolution is simultaneously reduced, meaning that the point spread function is increased. When the k-space sampling is incomplete, i.e. when k-space is under-sampled (which means that the azimuthal interval of the image points at the k-space boundary is greater than the radial interval of the image points due the number of projections being too low and a density compensation function is used that is adapted to complete sampling), the point spread function is non-local due to band artifacts. This means that the point spread function (PSF) has a sharp central portion with an artifact-free radius around the central part and sharp bands that begin outside of the artifact-free radius and run to the image border. These sharp bands of the PSF generate signal portions in the image far away from the associated image point. However, in the application to the present method this can mean that, due to the band artifacts, a signal intensity is indicated in a vessel in which no signal intensity is present, this shown intensity being due only to the strip artifacts. In contrast-intensified angiography acquisitions this means that vessels are shown with the intensity although these vessels had no contrast agent perfusion upon signal acquisition. These strip artifacts must consequently be reduced or suppressed. This is possible by selection of a suitable slope of the density compensation function. The density compensation function can generally be selected dependent on the spatial distance of the vessels to be depicted in the angiography exposure.

The density compensation function should compensate the acquisition with non-constant density in k-space, such that the density compensation function is advantageously selected in inverse proportion to the density of the sampling of k-space. If the density compensation function is not limited given large k-values (i.e. if high k-values, thus high signal frequencies, are suppressed in the image), the band artifacts in the image can likewise be suppressed. The limitation of the density compensation function at high k-values corresponds to a low-pass frequency filter that is applied to the image. This leads to two effects: first, the low-pass filtering expands the central portion of the density compensation function, thus leads to a signal smearing in the image. Second, it reduces the intensity of the band artifacts.

For this reason the density compensation function can advantageously be selected inversely proportional to the density of the sampling of k-space up to a predetermined value $k0$. The density compensation function for values of $k>k0$ can be selected either constant or with a negative slope. In the case of two-dimensional acquisition of k-space with radial projections, the density of acquired k-space decreases inversely proportional to the radius. This means that, for two-dimensional acquisition of k-space, the density compensation function can be selected proportional to k for values $k<k0$. In the case of three-dimensional acquisition of k-space with radial projections, the density for larger k-values or radii decreases quadratically. For this reason the density compensation function can be selected proportional to k squared given three-dimensional acquisition of k-space. This linear or quadratic increase of the density compensation function is now limited for values greater than $k0$; for example, the density compensation function can be selected constant or its slope decreases such that overall the filtering effect rises with increasing k-space values. This means that, for the values $k>k0$, the magnitude relative to the image is slowly pushed to 0 with increasing k.

Overall the density compensation function should at most be so strongly attenuated that the central portion of the point spread function is narrower than half of the interval of the vessels to be compared. In all cases, however, the density compensation function must be attenuated so far for large k-values that the band artifacts are sufficiently suppressed that that signal dynamics lying spatially far apart are not mixed. Depending on the geometry to be presented, the density compensation function can now be set such that either the image sharpness increases (meaning as good as if no density compensation were implemented, but this increases the band artifacts), or the band artifacts are more strongly suppressed, which leads to a stronger signal smearing in the image.

A smearing in the under-sampled MR images does not lead to an image smearing in the vessels in the MR exposures but rather leads to a smearing of the dynamic information in the MR exposures that were generated via multiplication of the under-sampled MR images with the averaged MR image. The smearing in the under-sampled MR images leads to a dispersion (spreading) of the dynamic information.

DESCRIPTION OF THE PREFERRED EMBODIMENTS

Figure 1:
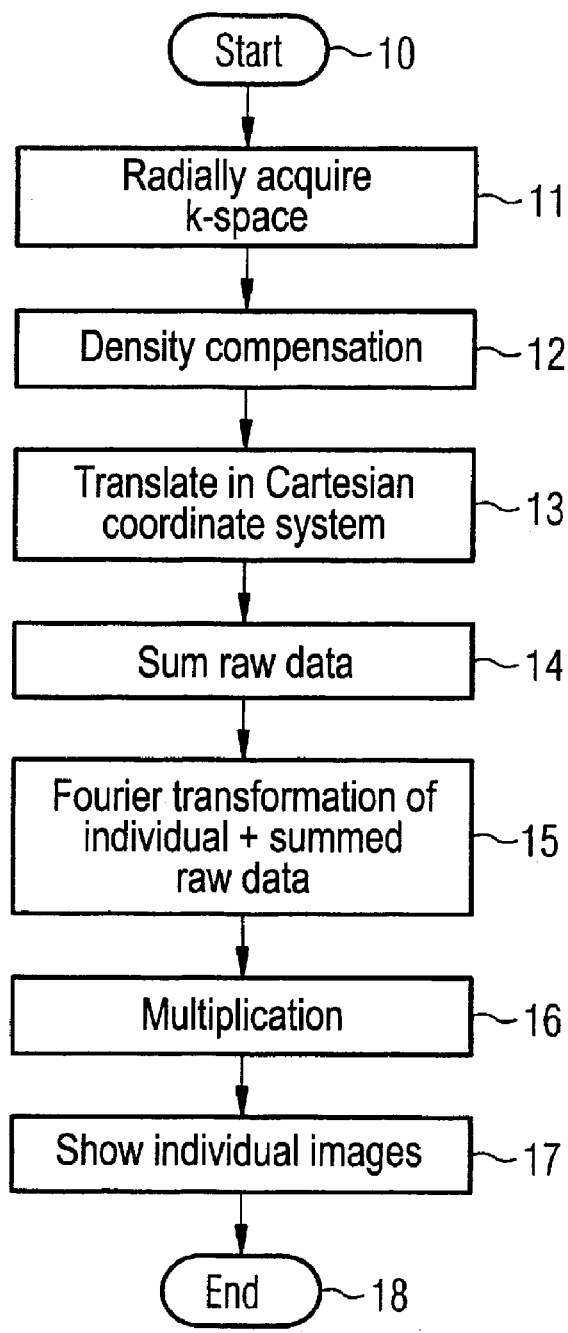
FIG. 1 is a flowchart of an embodiment of the inventive method for generation of temporally high-resolution MR angiography images.
Figure 2:
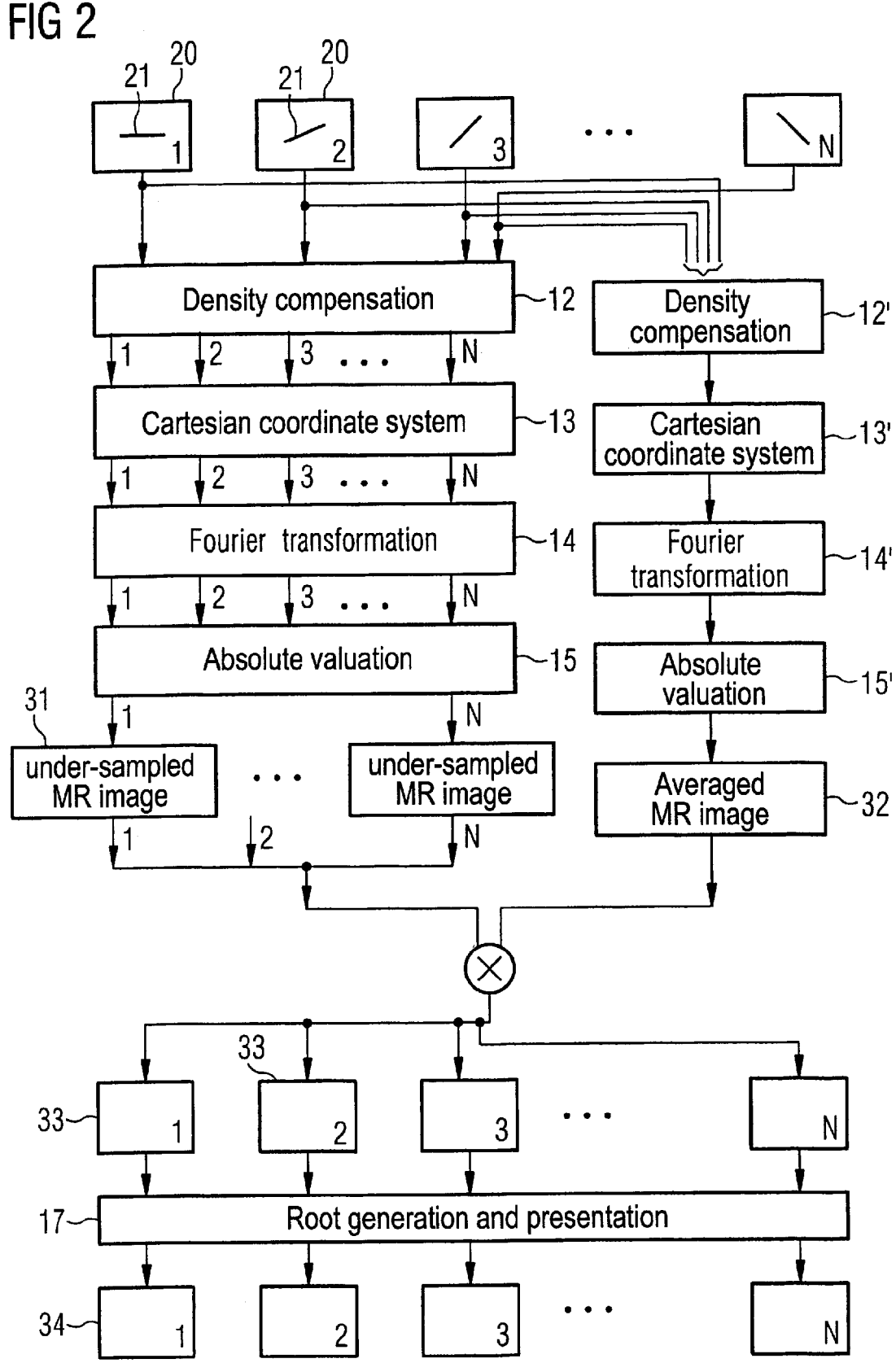
FIG. 2 schematically illustrates the processing of the individual raw data and images according to the method of FIG. 1.
Figure 3:
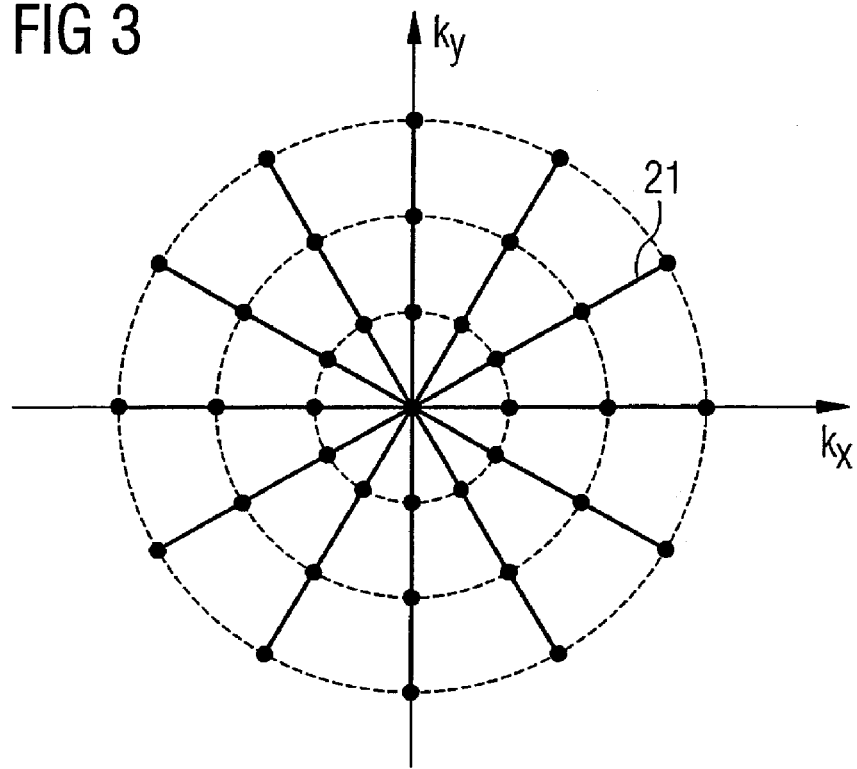
FIG. 3 schematically illustrates a radial two-dimensional acquisition scheme of k-space.

The inventive method is initially described on the basis of FIGS. 1 and 2. The method starts in a step 10. In a step 11 k-space or raw data space is filled with data with a radial acquisition technique, with a non-constant density of acquired k-space resulting from the radial acquisition technique. As shown in FIG. 2, in total N different under-sampled raw data are acquired. In the depiction selected in FIG. 2, each raw data set 20 exhibits a different trajectory 21, indicating that different projections are acquired for the various raw data. The two-dimensional, radially symmetrical exposure of k-space with various projections is shown as an example in FIG. 3. In this radially symmetrical exposure a measurement value is acquired at equidistant intervals along a projection 21 through the k-space center, with multiple projections 21 being used for each raw data set (for example a star as shown in FIG. 3). Different projections 21 are used for the various raw data sets 20 from FIG. 2, such that overall a large number of different k-space points are acquired. This means, for example, that stars (as in FIG. 3) rotated relative to one another are acquired for different raw data sets. As can also be seen in FIG. 3, the density of the acquired k-space points decreases proportional to a predetermined radial distance k in the two-dimensional case. For a three-dimensional acquisition of k-space, various projections through the k-space sphere are used. In this case the density of acquired k-space decreases proportional to R squared. The acquired nuclear magnetic resonance signal m(R) can be written as follows $$m(\vec{r}) = \sum_j W(\vec{k}_j) M(\vec{k}_j) e^{i2\pi \vec{k}_j \cdot \vec{r}} \quad (1)$$

for non-constant acquisition density of k-space. $W(k_j)$ is a weighting function that takes into account the non-constant density of the k-space points in the signal acquisition. In a radial acquisition technique more points are acquired in proximity to the k-space center than outside. This fact must be reflected in the density weighting. Given a two-dimensional acquisition technique, the density weighting function should run proportional to k in order to compensate the radial acquisition. In a three-dimensional radial acquisition technique, the density compensation function must be selected proportional to k squared in order to compensate the radial acquisition technique.

Figure 4:
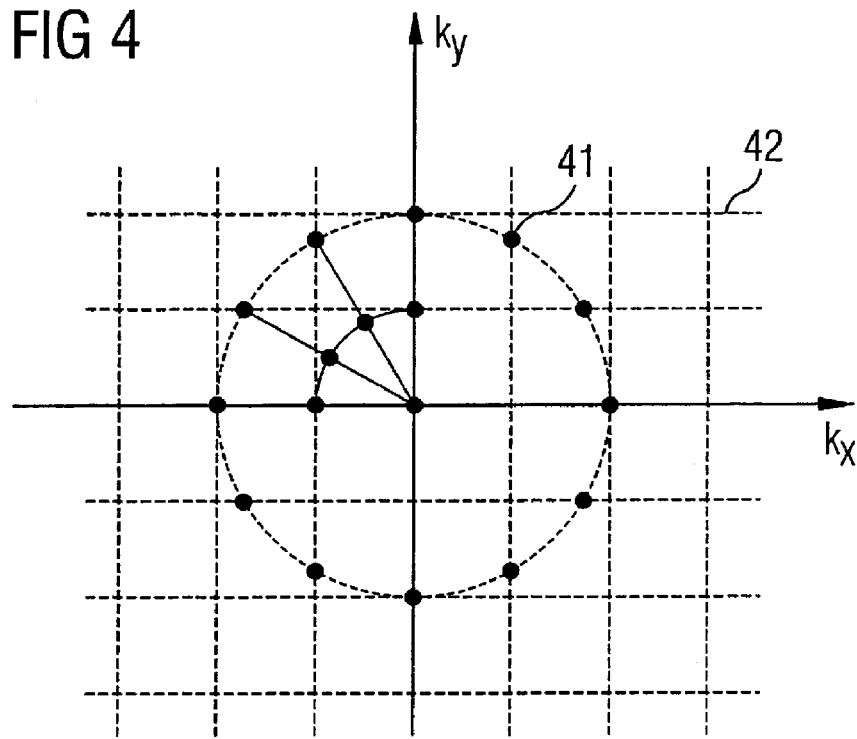
FIG. 4 shows radially acquired k-space points before the translation in a Cartesian coordinate system.

With regard to FIG. 1, the density compensation 12 is implemented after the step of the radial acquisition. As is to be recognized in FIG. 2, the density compensation is implemented for all N acquired, under-sampled radial raw data. The precise appearance of the density compensation function is specified in further detail in the further course of the application. After the density compensation by regridding (i.e. the translation of the acquired raw data points into a Cartesian coordinate system) ensues in step 13. FIG. 4 shows an example of how the raw data points are arranged for a predetermined radial distance k in k-space given a radial acquisition technique. As can be seen in FIG. 4, for a radial acquisition technique the raw data points 41 do not lie on the intersection points of a Cartesian coordinate system (which is likewise shown dashed with 42 in FIG. 4). In order to be able to use fast image calculation methods such as the fast Fourier transformation (FFT), however, the data must be present in a Cartesian coordinate system. The individual data points 41 must consequently be carried over into a Cartesian coordinate system. The interpolation of the non-Cartesian k-space points on a Cartesian coordinate system is possible in different ways. One possible interpolation method is a method in which a radially acquired k-space point is respectively associated with the nearest Cartesian k-space point. This method is also known as "nearest neighbor regridding". Further methods, known as regridding methods, are known those skilled in the art, such that they do not need to be described in detail herein. For example, the use of "Kaiser-Bessel window regridding" or any other interpolation methods is possible in order to bring the individual k-space points 41 into a Cartesian format.

As can be seen in FIG. 2, in a further step the individual raw data sets 20 are combined into an averaged raw data set, wherein this raw data set comprises the raw data of all individual raw data sets 20. This raw data set is no longer under-sampled since it comprises a much greater number of raw data points than the individual data sets 20. A density compensation is likewise implemented in step 12' with this averaged raw data set. The density compensation is designated with 12' in order to emphasize that the density compensation 12' is different from the density compensation of the individual raw data sets 12. A much greater number of projections are used in the density compensation 12'. Furthermore, the density compensation 12' enables a significantly higher spatial resolution. The translation into a Cartesian coordinate system likewise ensues in a step 13' analogous to the step 13. The translated, averaged raw data are Fourier-transformed in a step 14'. This Fourier transformation is also executed on the individual translated raw data sets in step 14. Finally, the absolute value formation of the Fourier-transformed data sets ensues in steps 15 and 15', respectively. The absolute value formation in steps 15 and 15' produces N under-sampled MR images 31 and to an averaged MR image 32. Each under-sampled MR image is then multiplied pixel-by-pixel with the averaged MR image 32 in a next step. This multiplication then leads to a sum of N MR images 33 with good spatial and temporal resolution. A non-linear scaling step subsequently follows, preferably a root generation for presentation of the temporally high-resolution MR angiographs 34.

The time curve of the contrast agent respectively arises through the under-sampled MR images 31. The position of the vessel to be depicted (or, respectively, the information for this) is comprised in an averaged MR image 32. The temporally high-resolution images 33 are obtained via multiplication of the individual under-sampled MR images with the averaged MR image. The images 31 can consequently be viewed as a mask that is applied to the averaged MR image. This mask contains the information of how the time curve of the signal intensity is in the individual vessels. However, due to multiplication with the averaged MR image the information is shown only where signal intensity can be present at all, namely in the vessels and not in the empty space around the vessels. The individual MR images can finally be shown in step 17 by the square root of the multiplied images being presented. The method ends in step 18.

The density compensation function is now discussed in detail in the following. If a density compensation function proportional to k is used given a radial sampling scheme in two dimensions, the fact of the radial acquisition technique can be ideally compensated. As was explained in connection with the individual under-sampled raw data sets 20, these are strongly under-sampled, which means that far fewer data points are acquired than are necessary under consideration of the Nyquist theorem in order to obtain an MR image with a resolution like the MR images 32 and 33. This under-sampling leads to a point spread function with a sharp central portion with an artifact-free radius around the central part and sharp bands outside of the artifact-free radius that run up to the image boundary. However, these band artifacts would lead to false information given the multiplication of the images 31 and 32. For this reason these band artifacts must be minimized. In k-space large k-space values represent high signal frequencies that are responsible for the resolution in the MR images while small k-space values are responsible for the contrast in the MR image. If the density compensation function W(k) from equation (1) is now limited for larger k-values, this means that the high k-values are suppressed in the image. If, for example, the density compensation function for k is selected greater than a predetermined value k0=constant, the filter effect increases with rising k, meaning that for k>k0 the contribution to the image by rising k is slowly pushed to 0. For k-values greater than k0, the density compensation function can be selected constant.

For example, for two-dimensional acquisitions W(k) is selected as follows:

$$W(k) \alpha \begin{cases} k \text{ for } k \leq k_0 \\ \text{constant for } k > k_0 \end{cases} \quad (2)$$

For a three-dimensional acquisition technique W(k) can read:

$$W(k) \alpha \begin{cases} k^2 \text{ for } k \leq k_0 \\ \text{constant for } k > k_0 \end{cases} \quad (3)$$

Instead of k=constant for k>k0, the density compensation function can also be selected such that it slowly goes to 0 for larger k.

$$W(k) \alpha \begin{cases} k \cdot \left(0.5 + \cos\left(\frac{k}{k_0} \cdot \prod\right)\right) \text{ for } k \leq k_0 \\ 0 \text{ for } k > k_0 \end{cases} \quad (4)$$

is given as a further possibility of the selection of the density compensation function.

In the last example k was multiplied with the Hanning filter for $k \leq k_0$.

The operating personnel can now adjust the density compensation dependent on the application. A selection must hereby be made between signal-to-noise ratio and spatial resolution. If the slope of the density compensation function is reduced, the signal-to-noise ratio in the image is increased and the band artifacts are reduced, however also the spatial resolution. Without density compensation function, i.e. given constant density compensation function, the largest signal-to-noise ratio is achieved via the lowest spatial resolution. The density compensation function can now be varied dependent on the vessel structure to be depicted.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for generating magnetic resonance exposures comprising the steps of:
    from a subject containing a structure to be depicted in a magnetic resonance image, said structure having a geometry associated therewith, acquiring a plurality of under-sampled magnetic resonance raw data sets with a non-constant density in k-space;
    compensating the respective magnetic resonance raw data sets with respect to said non-constant density, dependent on the geometry of the structure to be depicted, thereby obtaining a plurality of density-compensated, under-sampled magnetic resonance raw data sets;
    translating the density-compensated, under-sampled magnetic resonance raw data sets into a Cartesian coordinate system, thereby obtaining translated magnetic resonance raw data sets;
    Fourier transforming the translated magnetic resonance raw data sets to obtain under-sampled magnetic resonance images in three-dimensional space;
    generating an averaged magnetic resonance image as an average of a plurality of the under-sampled magnetic resonance raw data sets; and
    generating a magnetic resonance exposure of the subject, depicting said structure, by multiplying the under-sampled magnetic resonance images with the averaged magnetic resonance image.

2. A method as claimed in claim 1 comprising acquiring said magnetic resonance raw data sets in k-space in radial projections.

3. A method as claimed in claim 2 comprising employing different radial projections in k-space respectively for different ones of said under-sampled magnetic resonance raw data sets.

4. A method as claimed in claim 1 comprising compensating said density before translating the magnetic resonance raw data sets into the Cartesian coordinate system.

5. A method as claimed in claim 1 comprising executing both compensation of said density and translation into a Cartesian coordinate system in k-space.

6. A method as claimed in claim 1 wherein multiplication of said under-sampled MR images with said averaged MR image produces a multiplication product, and non-linearly scaling said multiplication product.

7. A method as claimed in claim 1 comprising compensating said density using a density compensation function having a slope that changes dependent on the structure to be depicted.

8. A method as claimed in claim 7 wherein said structure to be depicted comprises vessels to be depicted in an angiography exposure, and comprising selecting said density compensation function dependent on a spatial distance of the vessels from each other.

9. A method as claimed in claim 7 comprising selecting said density compensation function to be inversely proportional to a density of the sampling in k-space.

10. A method as claimed in claim 9 comprising acquiring said magnetic resonance raw data sets in k-space in respective different radial projections each exhibiting a radial distance, and selecting said density compensation function to be inversely proportional to the density of sampling in k-space up to a predetermined value of said radial distance.

11. A method as claimed in claim 10 comprising selecting said density compensation function to be constant or to have a negative slope for projection data sets respectively having a radial distance that is more than said predetermined value.

12. A method as claimed in claim 7 comprising acquiring said magnetic resonance raw data sets in two-dimensional k-space with respectively different radial projections, each having a radial distance associated therewith, and selecting said compensation function to be proportional to said radial distance.

13. A method as claimed in claim 7 comprising acquiring said magnetic resonance raw data sets in the three-dimensional k-space with respectively different radial projections, each having a radial distance associated therewith, and selecting said density compensation function to be proportional to the square of said radial distance.

14. A method as claimed in claim 7 comprising acquiring said magnetic resonance raw data sets in radial projections in k-space, each having a radial distance associated therewith, and setting said density compensation function to be equal to zero for radial distances that is more than a predetermined value.

15. A method as claimed in claim 7 wherein said structure to be depicted is a vessel structure in an angiography exposure, said vessels having a distance therebetween, and wherein said data in k-space exhibit a point spread function having a central region, and comprising selecting said density compensation function so that said central region of said point spread function is narrower than one-half of said distance.

16. A method as claimed in claim 1 comprising administering contrast agent to the subject at least prior to acquiring said magnetic resonance raw data sets, and generating contrast agent-intensified angiography images as said magnetic resonance images.

* * * * *